United States Patent [19]

Sanderson et al.

[11] Patent Number: 4,922,033

[45] Date of Patent: May 1, 1990

[54] PREPARATION OF TERTIARY BUTYL ALCOHOL BY THE CATALYTIC DECOMPOSITION OF TERTIARY BUTYL HYDROPEROXIDE

[75] Inventors: John R. Sanderson, Leander; John F. Knifton; Edward T. Marquis, both of Austin, all of Tex.

[73] Assignee: Texaco Inc., White Plains, N.Y.

[21] Appl. No.: 94,171

[22] Filed: Sep. 8, 1987

[51] Int. Cl.$^5$ .................. C07C 31/12; C07C 29/132; C07C 29/88; C07C 27/04

[52] U.S. Cl. .................. 568/909.8; 568/910; 568/914; 568/922; 568/571; 502/167

[58] Field of Search .............. 568/910, 840, 571, 914, 568/922, 909.8; 502/167

[56] References Cited

U.S. PATENT DOCUMENTS

| | | |
|---|---|---|
| 3,360,585 | 12/1967 | Winnick .............................. 568/840 |
| 3,505,360 | 4/1970 | Allison et al. ....................... 568/840 |
| 4,508,923 | 4/1985 | Taylor et al. ........................ 568/840 |
| 4,547,598 | 10/1985 | Sanderson et al. ................. 568/840 |
| 4,551,553 | 11/1985 | Taylor et al. ........................ 568/840 |

*Primary Examiner*—Vivian Garner
*Attorney, Agent, or Firm*—Jack H. Park; Kenneth R. Priem; Carl G. Ries

[57] ABSTRACT

A tertiary butyl hydroperoxide feedstock, such as one prepared by the reaction of isobutane with molecular oxygen comprising tertiary butyl hydroperoxide dissolved in tertiary butyl alcohol, is charged to a catalytic decomposition zone where the tertiary butyl hydroperoxide is catalytically decomposed in the presence of a soluble ruthenium catalyst compound promoted with a bidentate ligand to provide a decomposition reaction product characterized by a high conversion rate and a high selectivity of tertiary butyl hydroperoxide to tertiary butyl alcohol.

7 Claims, No Drawings

PREPARATION OF TERTIARY BUTYL ALCOHOL BY THE CATALYTIC DECOMPOSITION OF TERTIARY BUTYL HYDROPEROXIDE

BACKGROUND OF THE INVENTION

1. Field of the Invention

This invention relates to the catalytic decomposition of tertiary butyl hydroperoxide. More particularly, this invention relates to a method for the preparation of tertiary butyl alcohol by the catalytic decomposition of tertiary butyl hydroperoxide. Still more particularly, this invention relates to a method wherein a soluble ruthenium catalyst compound promoted with a bidentate ligand is used to catalyze the substantially selective decomposition of tertiary butyl hydroperoxide to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

The metal phthalocyanines are known compounds, described for example in the ACS Monograph Series by F. H. Moser and A. L. Thomas entitled "Phthalocyanine Compounds" (Rhinehold Publishing Corp.).

Williams et al. U.S. Pat. No. 3,816,548 is directed to a liquid phase oxidation process for oxidizing an isoparaffin hydrocarbon such as isobutane to an alcohol such as tertiary butyl alcohol in the presence of certain metal phthalocyanine catalysts.

Klein in U.S. Pat. No. 3,472,876, discloses the use of cobalt diimine chelates to catalyze the reaction of oxygen with an olefin to form an olefin epoxide.

Quin U.S. Pat. No. 2,854,487 discloses a process wherein isopropyl benzene hydroperoxides are catalytically decomposed to form carbinols in the presence of hydrogen and a catalyst composed of palladium supported on activated alumina.

Grane U.S. Pat. No. 3,474,151 discloses that tertiary butyl alcohol starts to dehydrate at 450° C. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–350° F. at a pressure lower than the pressure in the oxidation zone. The tertiary butyl alcohol can be further subjected to a cleanup treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

When isobutane is reacted with molecular oxygen, the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

A listing of the components present in a representative reaction product, and their nominal boiling points is given in Table A.

TABLE A

| Component | NBP (°C.) |
| --- | --- |
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl hydroperoxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S.

Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

In accordance with the present invention, isobutane is reacted with oxygen in an oxidation zone to provide an oxidation product comprising a solution of tertiary butyl hydroperoxide in unreacted isobutane. A catalyst may be present to catalyze the reaction of the oxygen with the isobutane if desired.

A suitable feedstock is used, such as one prepared by the oxidation of isobutane with molecular oxygen to provide an oxidation reaction product containing a solution of tertiary butyl hydroperoxide in unreacted isobutane. The feedstock may comprise tertiary butyl hydroperoxide dissolved in tertiary butyl alcohol which is recovered from the oxidation reaction product. The feedstock is charged to a catalytic decomposition zone wherein the tertiary butyl hydroperoxide is decomposed in the presence of a soluble ruthenium catalyst compound promoted with a bidentate ligand to provide a decomposition reaction product characterized by a high conversion rate and a high selectivity of tertiary butyl hydroperoxide to tertiary butyl alcohol.

The tertiary butyl alcohol will not be the only decomposition product that is formed. A minor amount of ditertiary butyl peroxide will also be formed together with other oxygen-containing materials such as those listed above.

The tertiary butyl alcohol that is recovered from the decomposition reaction mixture will be contaminated with ditertiary butyl peroxide and other oxygenated impurities.

The ditertiary butyl peroxide can be recovered, if desired, by a process such as the process disclosed in copending Sanderson et al. U.S. patent application Ser. No. 06/945,628, filed Dec. 23, 1986, and entitled "Recovery of Purified Ditertiary Butyl Peroxide" or the process disclosed in copending application Ser. No. 06/945,629, filed Dec. 23, 1986 by Sanderson et al., and entitled "Ditertiary Butyl Peroxide Recovery", now U.S. Pat. No. 4,810,809.

If desired, the ditertiary butyl peroxide and other contaminants may be removed from the tertiary butyl alcohol product by a catalytic purification process such as, for example, the purification process disclosed in copending Sanderson et al. U.S. patent application Ser. No. 06/836,798, filed Mar. 6, 1986, and entitled "Removal of Peroxide Contaminants from Tertiary Butyl Alcohol Using a Nickel Catalyst", now abandoned or by a purification process disclosed in copending Sanderson et al. U.S. patent application Ser. No. 06/926,159, filed Nov. 3, 1986, and entitled "Catalytic Removal of Peroxide Contaminants from Tertiary Butyl Alcohol", now U.S. Pat. No. 4,742,179, issued May 3, 1988 or by the process disclosed in copending Sanderson et al. application Ser. No. 06/932,822, filed Nov. 20, 1986, and entitled "Catalytic Decomposition of Impurities in Tertiary Butyl Alcohol", now issued as U.S. Pat. No. 4,705,903, issued Nov. 10, 1987 or, as yet another example, by the process disclosed in copending Sanderson et al. U.S. patent application Ser. No. 07/004,508, filed Jan. 30, 1987, and entitled "Catalyst for Removing Peroxide Contaminants from Tertiary Butyl Alcohol", now U.S. Pat. No. 4,873,380.

DESCRIPTION OF THE PROCESS OF THE PRESENT INVENTION

The starting materials for the process of the present invention are a tertiary butyl hydroperoxide feedstock, a soluble ruthenium catalyst, a bidentate ligand and a solvent.

The ruthenium-containing compounds employed as a catalyst may take many different forms. For instance, the ruthenium may be added to the reaction mixture in an oxide form, as in the case of, for example, ruthenium (IV) oxide hydrate, anhydrous ruthenium (IV) dioxide and ruthenium (VIII) tetraoxide. Alternatively, it may be added as the salt of a mineral acid, as in the case of ruthenium (III) chloride hydrate, ruthenium (III) bromide, ruthenium (III) iodide, tricarbonylruthenium nitrate, or as the salt of a suitable organic carboxylic acid, for example, ruthenium (III) acetate, ruthenium naphthenate, ruthenium valerate and ruthenium complexes with carbonyl-containing ligands such as ruthenium (III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_2(CO)_{12}$, and substituted carbonyl species such as the tricarbonylruthenium (II) chloride dimer, $(Ru(CO)_3Cl_2)_2$.

Ruthenium-containing compounds include oxides of ruthenium, ruthenium salts of an organic carboxylic acid and ruthenium carbonyl or hydrocarbonyl derivatives. Among these are ruthenium (IV) dioxide hydrate, ruthenium (VIII) tetraoxide, anhydrous ruthenium (IV) oxide, ruthenium acetate, ruthenium propionate, ruthenium (III) acetylacetonate, and triruthenium dodecacarbonyl.

Additional examples of ruthenium compounds include ruthenium octoate, ruthenium laurate, ruthenium stearate, ruthenium linoleate, ruthenium nitrate, ruthenium sulfate and ruthenium carbonyl.

Other representative examples of soluble ruthenium catalysts that may be used alone or in admixture include ruthenium salts of carboxylic acids produced in the course of oxidation of the precursor hydrocarbon from which the organic hydroperoxide may have been obtained. Representative examples of organic acids which may be produced in the course of oxidation of the hydrocarbon starting material precursor to the organic hydroperoxide include: acetic, formic and isobutyric acids.

Bidentate ligands of the following general structure may be used:

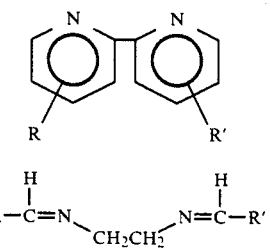

wherein R and R' may be the same or diferent and represent hydrogen, methyl, ethyl, propyl, phenyl or chlorophenyl.

Representative examples of amine ligands include amines such as 2,2'-dipyridyl, bis(salicylidene) ethylenediamine, 2,2'-dipicoline, bis(methylsalicylidene) ethylenediamine, bis(ethylsalicylidene) ethylenediamine, bis(propylsalicylidene) ethylenediamine, etc.

From about 0.01 to about 10 parts by weight of bidentate ligand should be employed per part of ruthenium catalyst, e.g. from about 1 to about 3 parts by weight, and more preferably, from about 0.1 to about 2 parts.

The concentration of the catalyst in the liquid phase may vary widely. From about 0.001 to about 5 wt. %, based on the weight of the t-butyl hydroperoxide, of a soluble ruthenium catalyst compound and about 1 to 3 parts by weight, based on the weight of the ruthenium compound, of a bidentate ligand may be added to the charge stock. In general, the catalyst system of the present invention may advantageously be employed in amounts ranging from about 0.01 ppm to about 5,000 ppm of ruthenium.

The solvent to be used in practicing the process of the present invention may be any suitable organic solvent in which tertiary butyl hydroperoxide is soluble at least to an extent sufficient to provide a solution containing from about 5 to about 30 wt. % of tertiary butyl hydroperoxide. A preferred solvent is isobutane and a still more preferred solvent is tertiary butyl alcohol or a mixture thereof with isubutane. In accordance with the most preferred embodiment of the present invention, the charge material for the process will comprise about a 5 to about a 30 wt. % solution of tertiary butyl hydroperoxide and tertiary butyl alcohol.

The process of the present invention may be conducted batchwise in kettles or by continuously passing the reactants through a reactor.

The catalytic decomposition of the tertiary butyl hydroperoxide is preferably conducted at a temperature within the range of about 25° to about 125° C. and, more preferably, at a temperature within the range of about 30 to about 80° C. The reaction is preferably conducted at autogenous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours.

In accordance with the most preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, and some tertiary butyl alcohol. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide. If the tertiary butyl hydroperoxide concentration is excessive, additional tertiary butyl alcohol may be added.

The solvent solution of tertiary butyl hydroperoxide in organic solvents (e.g., tertiary butyl alcohol solvent solution of tertiary butyl hydroperoxide) is then charged to a catalytic hydroperoxide decomposition zone where it is brought into contact with a catalyst composed of a soluble ruthenium compound and a bidentate ligand to substantially selectively convert the tertiary butyl hydroperoxide to tertiary butyl alcohol with high yields and selectivities.

As indicated, the catalytic decomposition of the tertiary butyl hydroperoxide in the catalytic hydroperoxide decomposition reaction zone may suitably be conducted at a temperature within the range of about 25° to 125° C. (and more preferably from about 30° to about 80° C.) at autogenous pressure or if desired at a superatmospheric pressure up to 1000 psi9. for a contact time within the range of about 0.5 to about 10 hours.

The reaction product from the tertiary butyl hydroperoxide decomposition step may then be fractionated in any suitable manner, such as, for example, in the manner shown in the process disclosed in above identified copending U.S. patent application Ser. No. 06/945,628 filed Dec. 23, 1986. In accordance with a process recovery sequence of this nature, both the tertiary butyl alcohol and the ditertiary butyl peroxide will be recovered in purified form as products of the reaction.

Alternately, a crude tertiary butyl alcohol product stream contaminated with ditertiary butyl peroxide and other contaminants may be obtained which will then be further treated either thermally, in accordance with the process of the Grane et al. U.S. patents, or catalytically by one of the processes disclosed in the copending Sanderson et al. patent applications to convert the ditertiary butyl peroxide to tertiary butyl alcohol and to otherwise significantly reduce the level of contamination of the other oxygencontaining impurities.

SPECIFIC EXAMPLES

The invention will be further illustrated by the following specific examples which are given by way of illustration and not as limitations on the scope of this invention.

Procedure: Tube Experiments

A 150-ml Fisher-Porter pressure tube equipped with pressure gauge, rupture disk, and shut-off valve was charged with 15.0 g of a 20% TBHP solution in TBA, and catalyst(s). The tube was suspended in a constant temperature bath (+or −0.2° C.) for the desired period of time at the required temperature. The tube was shaken from time to time during the run. At the end of the run, the tube was placed in cold water (15°–20° C.) for 15 minutes. The pressure was then slowly released. The contents were analyzed by GC. The results are shown in the attached Table I.

TABLE I

Decomposition of tert-Butylhydroperoxide in the Presence of a Homogeneous Catalyst System Containing Ruthenium and a Bidentate Ligand

| Notebook No. | Catalyst(s)[a] | Time (Hr) | Temp (°C.) | TBHP % | Wt. % TBA | Acetone | MeOH | DTBP |
|---|---|---|---|---|---|---|---|---|
| 6224-63 | Ru(AcAc)₃ [.005 g] | 1.0 | 100.0 | 0.027 | 95.447 | 2.570 | 0.405 | 0.601 |
| 6224-70 | Ru(AcAc)₃ [.005 g] | 1.5 | 80.0 | 0.031 | 95.903 | 1.917 | 0.218 | 0.860 |
| 6224-73 | Ru(AcAc)₃ [.005 g] | 2.0 | 80.0 | 0.031 | 95.956 | 1.883 | 0.209 | 0.890 |
| 6224-75 | Ru(AcAc)₃ [.005 g] | 4.0 | 60.0 | 0.017 | 96.183 | 1.427 | 0.113 | 1.317 |
| 6224-77 | Ru(AcAc)₃ [.005 g] | 1.0 | 60.0 | 0.024 | 96.133 | 1.479 | 0.118 | 1.244 |
| 6225-27[b] | Ru(AcAc)₃ [.005 g] Cr(AcAc)₃ [.01 g] | 2.0 | 60.0 | 0.051 | 96.370 | 1.410 | 0.097 | 1.135 |
| 6224-100 | Ru(AcAc)₃ [.005 g] DIPY [.03 g] | 2.0 | 60.0 | 1.373 | 96.272 | 1.058 | 0.062 | 0.416 |
| 6225-02 | Ru(AcAc)₃ [.005 g] DIPY [.01 g] | 2.0 | 60.0 | 0.599 | 96.165 | 1.075 | 0.065 | 1.244 |
| 6225-03 | Ru(AcAc)₃ [.005 g] BSEDA [.01 g] | 2.0 | 60.0 | 0.128 | 96.423 | 1.190 | 0.069 | 1.327 |
| 6225-29 | Ru(AcAc)₃ [.01 g] BSEDA [.02 g] | 2.0 | 60.0 | 5.242 | 92.244 | 0.601 | 0.043 | 1.153 |
| 6225-30 | Ru(AcAc)₃ [.01 g] BSEDA [0.1 g] | 2.0 | 60.0 | 0.520 | 96.153 | 1.101 | 0.072 | 1.316 |
| 6225-36 | Ru(AcAc)₃ [.005 g] DIPY [.01 g] | 2.0 | 40.0 | 2.349 | 94.159 | 0.570 | 0.021 | 2.144 |
| — | Starting Material | | | 20.20 | 79.282 | 0.007 | 0 | 0.060 |

[a]AcAc = Acetylacetonate; DIPY = 2,2'-dipyridyl; BSEDA = bis (salicylidene)ethylenediamine
[b]U.S. Pat. No. 4,551,553 (ARCO)

With reference to the table, it will be noticed that the use of a soluble ruthenium catalyst promoted with an amine ligand resulted in an enhanced rate of decomposition of the tertiary butyl hydroperoxide as shown by the increased conversion for the given reaction time and an enhanced selectivity of the tertiary butyl hydroperoxide to tertiary butyl alcohol as compared with the use of a soluble ruthenium catalyst without an amine ligand or a binary mixture of a ruthenium compound with a chromium compound.

Having thus described our invention, what is claimed is:

1. In a method wherein a t-butyl hydroperoxide charge stock is brought into contact with a catalytically effective amount of a hydroperoxide decomposition catalyst in a hydroperoxide decomposition reaction zone in liquid phase with agitation to convert said t-butyl hydroperoxide to decomposition products, principally t-butyl alcohol, the improvement which comprises:
   (a) using, as said hydroperoxide decomposition catalyst, a soluble ruthenium catalyst compound promoted with a bidentate ligand,
   (b) recovering said t-butyl alcohol from the products of said hydroperoxide decomposition reaction, and
   (c) said bidentate ligand having the formula:

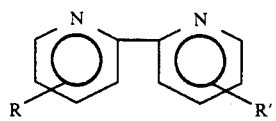

wherein R and R' may be the same or different and are selected from the group consisting of hydrogen, methyl, ethyl, propyl, phenyl and chlorophenyl or

wherein R and R' may be the same or different and are selected from the group consisting of hydrogen, methyl, ethyl, propyl, phenyl, chlorophenyl,

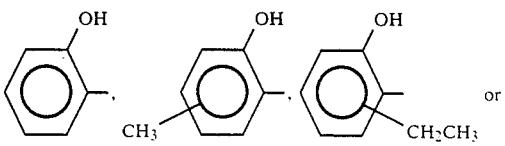

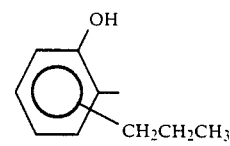

2. In a method wherein a solution of a t-butyl hydroperoxide charge stock in t-butyl alcohol is brought into contact with a catalytically effective amount of a hydroperoxide decomposition catalyst in a hydroperoxide decomposition reaction zone in liquid phase with agitation under hydroperoxide decomposition reaction conditions to convert said t-butyl hydroperoxide to decomposition products, principally t-butyl alcohol, the improvement which comprises:
   (a) preparing a t-butyl alcohol solution of a soluble ruthenium catalyst compound and a bidentate ligand selected from the group consisting of 2,2'-dipyridyl and bis(salicylidene)ethylenediamine,
   (b) charging a t-butyl alcohol solution of said ruthenium catalyst and said ligand to said hydroperoxide decomposition reaction zone as said hydroperoxide decomposition catalyst, and
   (c) recovering said t-butyl alcohol from the products of said hydroperoxide decomposition reaction.

3. A method as in claim 2 wherein the soluble ruthenium catalyst compound is ruthenium acetylacetonate and the bidentate ligand is 2,2'-dipyridyl.

4. A method as in claim 2 wherein the soluble ruthenium catalyst compound is ruthenium acetylacetonate and the bidentate ligand is bis(salicylidene)ethylenediamine.

5. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, wherein unreacted isobutane is continuously separated from said initial reaction mixture to provide a charge stock comprising a solution of said t-butyl hydroperoxide in said t-butyl alcohol, containing from about 5 to about 30 wt. % of t-butyl hydroperoxide, wherein said charge stock is continuously charged to a hydroperoxide decomposition zone, and wherein a catalytic hydroperoxide decomposition reaction is continuously conducted in said decomposition reaction zone to convert said t-butyl hydroperoxide to decomposition products, principally t-butyl alcohol, to provide a hydroperoxide conversion product, the improvement which comprises:
(a) adding from about 0.001 to about 5 wt. %, based on the weight of the t-butyl hydroperoxide of a soluble ruthenium catalyst compound and about 1 to about 3 parts by weight, based on the weight of the ruthenium compound of a bidentate ligand to said charge stock as said hydroperoxide decomposition catalyst,
(b) conducting said hydroperoxide decomposition reaction in the presence of said thus-prepared hydroperoxide decomposition catalyst in said hydroperoxide decomposition zone in liquid phase with agitation under reaction conditions including a temperature within the range of about 30° to about 80° C. and autogenous pressure,
(c) continuously removing a stream of said hydroperoxide conversion product from said hydroperoxide conversion zone, and
(d) continuously recovering t-butyl alcohol from said stream of said hydroperoxide conversion product,
(e) said bidentate ligand having the formula:

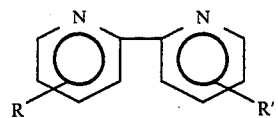

wherein R and R' may be the same or different and are selected from the group consisting of hydrogen, methyl, ethyl, propyl, phenyl and chlorophenyl or

wherein R and R' may be the same or different and are selected from the group consisting of hydrogen, methyl, ethyl, propyl, phenyl, chlorophenyl,

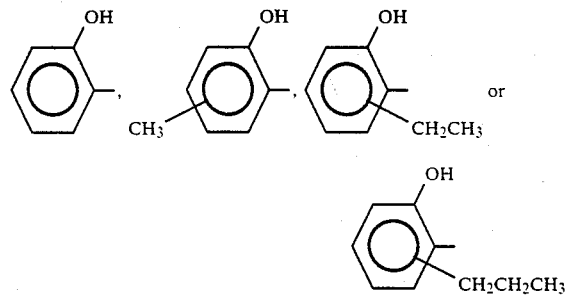

6. A method as in claim 5 wherein the soluble ruthenium catalyst compound is ruthenium acetylacetonate and the bidentate ligand is 2,2'dipyridyl.

7. A method as in claim 5 wherein the soluble ruthenium catalyst compound is ruthenium acetylacetonate and the bidentate ligand is bis(salicylidene)ethylenediamine.

* * * * *